US006194465B1

(12) United States Patent
Flitter et al.

(10) Patent No.: US 6,194,465 B1
(45) Date of Patent: Feb. 27, 2001

(54) BENZAMIDE THERAPEUTICS FOR THE TREATMENT OF INFLAMMATORY BOWEL DISEASE

(75) Inventors: William D. Flitter, Mountain View; William A. Garland, Los Gatos; Ian Irwin, Palo Alto, all of CA (US)

(73) Assignee: Centaur Pharmaceuticals, Inc., Sunnyvale, CA (US)

( * ) Notice: Subject to any disclaimer, the term of this patent is extended or adjusted under 35 U.S.C. 154(b) by 0 days.

(21) Appl. No.: 09/313,272

(22) Filed: May 18, 1999

Related U.S. Application Data

(60) Provisional application No. 60/086,361, filed on May 19, 1998.

(51) Int. Cl.[7] .................................................. A61K 31/165
(52) U.S. Cl. ........................................... 514/619; 514/617
(58) Field of Search ...................................... 514/619, 617

(56) References Cited

U.S. PATENT DOCUMENTS

| 5,036,097 |   | 7/1991  | Floyd et al.    | 514/400 |
| 5,292,746 |   | 3/1994  | Carr et al.     | 514/278 |
| 5,472,983 | * | 12/1995 | Flitter et al.  | 514/599 |
| 5,643,965 | * | 7/1997  | Flitter et al.  | 514/619 |
| 5,658,953 | * | 8/1997  | Flitter et al.  | 514/616 |
| 5,659,082 | * | 8/1997  | Flitter et al.  | 564/166 |
| 5,756,548 | * | 5/1998  | Flitter et al.  | 514/616 |
| 5,804,589 | * | 9/1998  | Bouyssou et al. | 514/331 |
| 5,907,061 | * | 5/1999  | Flitter et al.  | 564/142 |
| 5,914,350 | * | 6/1999  | Flitter et al.  | 514/619 |

FOREIGN PATENT DOCUMENTS

| 0 474 403 A1 | 11/1992 | (EP) . |
| 92/22290 | 12/1992 | (WO) . |
| 95/11227 | 4/1995 | (WO) . |
| 95/28153 | 10/1995 | (WO) . |
| 96/31462 | 10/1996 | (WO) . |
| 97/00680 | 1/1997 | (WO) . |
| 97/30990 | 8/1997 | (WO) . |
| 97/39751 | 10/1997 | (WO) . |
| 99/20601 | 4/1999 | (WO) . |

OTHER PUBLICATIONS

Anana, RD et al. (1997) Synthesis and smooth–muscle calcium–channel effects of dialkyl 1.4–dihydro–2, 6–dimethy–4–aryl–3,5–pyridinedicarboxylates containing a nitrone moiety in the 4–aryl substituent, Arch. Pharm. (Weinheim, Ger.) 330: 53–58.

Bonner, GF (1996) Current medical therapy for inflammatory bowel disease, Southern Medical Journal, 89: 556–566.

Buettner, GR (1987) ESR Parameters of Spin Adducts, Free Radical Biology, 3:259–303.

Calkins, BM, Mendeloff, Al (1986) Epidemiology of Inflammatory Bowel Disease, Epidemiology Review 8: 60–90.

Cao, X. and Phillis, JW (1994) a–Phenyl–N–tert–butyl–nitrone Reduces Cortical Infarct and Edema in Rats Subjected to Focal Ischemia. Brain Res, 644: 267–272.

Carney, JM, Starke–Reed, PE Oliver, CN, Landrum, RW, Cheng, MS, Wu, JF and Floyd, RA (1991) Reversal or age–related increase in brain protein oxidation in enzyme activity, and loss in temporal and spatial memory by chronic administration of the spin–trapping compound N–tert–butyl–α–phenylnitrone. Proc. Natl. Acad. Sci., 88:3633–3636.

Castro, GA, Roy, SA, Stockstill, RD (1974) Trichinella Spiralis: Peroxidase Activity in Isolated Cells from the Rat Intestine, Exp. Parasitol., 36: 307–315.

Crotty, B. (1994) Ulcerative Colitis and Xenobiotic Metabolism, Lancet, 343:35–38.

Edamatsu, R, Mori,A., Packer, L (1995) The Spin Trap N–tert–α–phenyl–butylnitrone Prolongs the Life Span of the Senescence Accelerated Mouse, Biochem Biophys Res Comm 211: 847–849.

Elson, CO, Startor, RB, Tennyson, GS, Ridell, RH (1995), Experimental Models of Inflammatory Bowel Disease, Gastroenterology, 109: 1344–1367.

Floyd, RA and Carney, J., Nitrone Radical Traps (NRTs) Protect in Experimental Neurodegenerative Diseases, in Neuroprotective Approaches to the Treatment of Parkinson's Disease and Other Neurodegenerative Disorders (Olanow, CW, Jenner, P and Youssim E, Eds.) Academic Press, New York, in press.

Glickman, RM (1994) Inflammatory Bowel Disease in Harrison's Principles of Internal Medicine (McGraw Hill, New York, NY) Chapter 255: 1403–1416.

Greenwood–Van Maerveld, B, Tyler, KR, Johnson, AC, Peters, LJ, Flitter, W, Garland, W, Oklahoma Foundation for Digestive Research, Virginia Medical Center, Oklanhoma City, OK and Centaur Pharmaceuticals, Inc., Sunnyvale, CA, Anti–Inflammatory Effects of a Novel Antioxidant in Rats, XP–002117692, G4047.

Greenwood–Van Maerveld, B, Tyler, KR, Johnson, AC, Adesina, AM, Dunn, ST, Irwin, I, Garland, W, Oklahoma Foundation for Digestive Research, Virginia Medical Center, Oklahoma City, OK, CPI–1189, Protects Against Dextran Sulfate Sodium–Induced Colitis in Mice, XP–002117693, G3156.

Grisham MB, MacDermott, RP, Deitch EA (1990), Oxidant Defence Mechanisms in the Humam Colon, Inflammation, 14:669–680.

(List continued on next page.)

Primary Examiner—Jerome D. Goldberg
Assistant Examiner—Jennifer Kim
(74) Attorney, Agent, or Firm—Burns, Doane, Swecker & Mathis, LLP (57) ABSTRACT

Benzamides are disclosed to be useful for treating and preventing inflammatory bowel disease.

22 Claims, 5 Drawing Sheets

OTHER PUBLICATIONS

Hamburger, SA, McCay, PB (1989) Endotoxin–Induced Mortality in Rats is Reduced by Nitrones, *Circulatory Shock*, 29: 329–334.

Hanauer, SB, Baert, F. (1994) Medical Therapy of Inflammatory Bowel Disease, *Med Clin North Am*, 78: 1413–1426.

Hanauer, B. (1993) Medical Therapy of Ulcerative Colitis, *Lancet*, 342: 412–417.

Harris, ML, Schiller, HJ, Reilly, PM, Donowitz, M, Grisham, MB, Bulkley (1992), Free Radicals and Other Reactive Oxygen Metabolites in Inflammatory Bowel Disease: Cause, Consequence or Epiphenomenom, *Pharmacol. Ther.*, 53: 375–408.

Higa, A. McKnight, GW, Wallace, JL (1993) Attenuation of Epithelial Injury in Acute Experimental Colitis by Immunomodulators, *Eur. J. Pharmacol.* 239: 171–178.

Levin, B. (1992) Inflammatory Bowel Disease and Colon Cancer, *Cancer (Supplement)*, 70:1313–1316.

MacDermott, RP (1994) Alterations in the Mucosal System in Ulcerative Colitis and Crohn's Disease, *Med Clin North Am*, 78: 1207–1231.

McKechnie, K., Furman, BL, Paratt JR (1986), Modification by Oxygen Free Radical Scavengers of the Metabolic and Cardiovascular Effects of Endotoxin Infusion in Conscious Rats, *Circulatory Shock* 19: 429–439.

Miyajima, T., Kotake, Y. (1995) Spin Trapping Agent, Phenyl N–Tert_Butyl Nitrone, Inhibits Induction of Nitric Oxide Synthase in Endotoxin–Induced Shock in Mice, *Biochem Biophys Res Commun*, 215: 114–121.

Novelli, GP (1992) Oxygen Radicals in Experimental Shock: Effects of Spin–Trapping Nitrones in Ameliorating Shock Pathophysiology, *Critical Care Medicine*, 20: 499–507.

Oliver, CN, Starke–Reed, PE, Stadtman, ER, Carney, JM and Floyd, RA (1990) Oxidative Damage to Brain Proteins, Los of Glutamine Synthetase Activity and Production of Free Radicals During Ischemia Induced Injury to Gerbil Brain. *Proc. Natl. Acad. Sci. USA* 87: 5144–5147.

Progrebniak, HW, Merino, MJ, Hahn, SM, Mitchell, JB, Pass, HI (1992) Spin Trap Salvage from Endotoxemia: The Role of Cytokine Down–Regulation, *Surgery*, 112: 130–139.

Thomas, CE, Ohlweiler, DF, Carr, AA, Nieduzak, TR, Hay, DA, Adams, G, Vaz, R and Bernotas, RC (1995) Characterization of the Radical Trapping Activity of a Novel Series of Cyclic Nitrone Spin Traps, *Journal of Biological Chemistry*, 271: 3097–3104.

Wallace, JA, MacNaughton, WK, Morris, GP, Beck PL (1989) Inhibition of Leulotriene Synthesis Markedly Accelerates Healing in a Rat Model of Inflammatory Bowel Disease, *Gastroenterology*, 95: 29–35.

Winrow, VR, Winyard, PG, Morris, CJ, Blake, DR (1993) Free radicals in Inflammation: Second Messengers and Mediators of Tissue Destruction, *Br Med Bull* 49: 506–522.

Yamada, T, Marshall, S, Specian, RD, Grisham, MB (1992) A Comparative Analysis of Two Models of Colitis in Rats, *Gastroenterology*, 102: 1524–1534.

Zhao, Q., Pahlmark, K., Smith, M.–J., and Siesjo, B. (1994) DelayedTreatment with the Spin Trap a–phenyl–n–tert–butyl nitrone (PBN) Reduces Infarct Size Following Transient Middle Cerebral Artery Occlusion in Rats. *Acta Physiol. Scad.* 152: 349–350.

* cited by examiner

BENZAMIDE THERAPEUTICS FOR THE TREATMENT OF INFLAMMATORY BOWEL DISEASE

CROSS-REFERENCE TO RELATED APPLICATIONS

This application claims the benefit of U.S. patent application Ser. No. 60/086,361, filed May 19, 1998, the disclosure of which is incorporated herein by reference in its entirety.

BACKGROUND OF THE INVENTION

1. Field of the Invention

This invention relates to the treatment of inflammatory bowel disease. More specifically, it relates to methods and pharmaceutical compositions for the treatment and prophylaxis of IBD.

2. State of the Art

The term inflammatory bowel disease ("IBD") describes a group of chronic inflammatory disorders of unknown causes involving the gastrointestinal tract ("GI tract"). The prevalence of IBD in the US is estimated to be 200 per 100,000 population (approximately 500,000 people). Patients with IBD can be divided into two major groups, those with ulcerative colitis ("UC") and those with Crohn's disease ("CD").

In patients with UC, there is an inflammatory reaction primarily involving the colonic mucosa. The inflammation is typically uniform and continuous with no intervening areas of normal mucosa. Surface mucosal cells as well as crypt epithelium and submucosa are involved in an inflammatory reaction with neutrophil infiltration. Ultimately this situation typically progresses to epithelial damage with loss of epithelial cells resulting in multiple ulcerations, fibrosis, dysplasia and longitudinal retraction of the colon.

CD differs from UC in that the inflammation extends through all layers of the intestinal wall and involves mesentery as well as lymph nodes. CD may affect any part of the alimentary canal from mouth to anus. The disease is often discontinuous- severely diseased segments of bowel are separated from apparently disease-free areas. In CD the bowel wall thickens which can lead to obstructions. Fistulas and fissures are not uncommon.

Clinically, IBD is characterized by diverse manifestations often resulting in a chronic unpredictable course. Bloody diarrhea and abdominal pain are often accompanied by fever and weight loss. Anemia is not uncommon, as is severe fatigue. Joint manifestations ranging from arthralgia to acute arthritis as well as abnormalities in liver function are commonly associated with IBD. Patients with IBD have an increased risk of colon carcinomas compared to the general population. During acute "attacks" of IBD, work and other normal activity are usually impossible, and often a patient is hospitalized.

Although the cause of IBD remains unknown, several factors such as genetic, infectious and immunologic susceptibility have been implicated. IBD is much more common in Caucasian, especially those of Jewish descent. The chronic inflammatory nature of the condition has prompted an intense search for a possible infectious cause. Although agents have been found which stimulate acute inflammation, none has been found to cause the chronic inflammation associated with IBD. The hypothesis that IBD is an autoimmune disease is supported by the previously mentioned extraintestinal manifestation of IBD as joint arthritis, and the known positive response to IBD by treatment with therapeutic agents such as adrenal glucocorticoids, cyclosporine and azathioprine, which are known to suppress immune response. In addition, the GI tract, more than any other organ of the body, is continuously exposed to potential antigenic substances such as proteins from food, bacterial byproducts (LPS), etc.

Once the diagnosis has been made, typically by endoscopy, the goals of therapy are to induce and maintain a remission. The least toxic agents with which patients are typically treated are the aminosalicylates. Sulfasalazine (Azulfidine), typically administered four times a day, consists of an active molecule of aminosalicylate (5-ASA) which is linked by an azo bond to a sulfapyridine. Anaerobic bacteria in the colon split the azo bond to release active 5-ASA. However, at least 20% of patients cannot tolerate sulfapyridine because it is associated with significant side-effects such as reversible sperm abnormalities, dyspepsia or allergic reactions to the sulpha component. These side effects are reduced in patients taking olsalazine. Neither sulfasalazine nor olsalazine are effective for the treatment of small bowel inflammation. However, other formulations of 5-ASA have been developed which are released in the small intestine (e.g. mesalamine and asacol). Normally it takes 6–8 weeks for 5-ASA therapy to show full efficacy.

Patients who do not respond to 5-ASA therapy, or who have a more severe disease, are prescribed corticosteroids. However, this is a short term therapy and cannot be used as a maintenance therapy. Clinical remission is achieved with corticosteroids within 2–4 weeks, however the side effects are significant and include a Cushing goldface, facial hair, severe mood swings and sleeplessness. The response to sulfasalazine and 5-aminosalicylate preparations is poor in Crohn's disease, fair to mild in early ulcerative colitis and poor in severe ulcerative colitis. If these agents fail, powerful immunosuppressive agents such as cyclosporine, prednisone, 6-mercaptopurine or azathioprine (converted in the liver to 6-mercaptopurine) are tried. For Crohn's disease patients, the use of corticosteroids and other immunosuppressives must be carefully monitored because of the high risk of intra-abdominal sepsis originating in the fistulas and abscesses common in this disease. Approximately 25% of IBD patients will require surgery (colectomy) during the course of the disease.

Oxygen-derived free radicals such as HO●, the superoxide anion and other reactive oxygen species such as HOCl, have emerged as a common pathway of tissue injury in a wide variety of diseases whose underlying cause is an inappropriately vigorous and sustained immune response (failure to control or down regulate response to the initial, appropriate stimulus). Examples of other disease, in addition to IBD and arthritis, where this mechanism seems to be the operative cause are ARDS, septic shock, asthma, diabetes, multiple sclerosis, uveitis, etc. Typically both a cytokine-mediated immune response and a nonspecific inflammatory cascade are involved in the primary inappropriate response with both responses mediated through active oxygen species (oxidative stress). The inappropriate secondary response, also mediated through oxidative stress) may involve tissue damaging oxidation by neutrophils and tissue macrophages.

Various approaches have been taken to suppress this inappropriate inflammatory response. The efficacy of small molecule inhibitors of the various leukotriene, PAF and cyclooxygenase pathways have shown only limited efficacy, perhaps because blocking only one of many pathways does not provide a sufficiently large decrease in overall oxidative stress. The other approach has been the use of antibodies or cloned receptor molecules which target specific proteins in the inflammatory cascade such as IL-1, IL-6 or TNF-α. However, this approach is practical only for acute conditions like septic shock or ARDS where IV administration and antibody formation against the therapeutic protein is less of a concern. For a chronic condition like IBD, an orally active small molecule that is fully active when dosed once-a-day seems to be the ideal candidate.

Another approach to mitigating the oxidative stress resulting from an inflammatory response is to employ nitrone related therapeutics (NRTs). The prototype NRT is α-phenyl-t-butyl nitrone (PBN) shown below.

NRTs represent a new category of therapeutics with the inherent capacity to overcome the shortcomings of other previously studied compounds. PBN is relieved to trap a free radical (R●) by adding R as shown below with formation of the following more unreactive nitroxyl free radical.

Nitrones were first used as analytical tools capable of reacting with highly reactive radicals to yield free radical adducts that are much less reactive. In many cases, the free radical/NRT adduct complex is stable enough to allow in vivo isolation and quantitation using electron spin resonance (ESR). The concept of using nitrones as therapeutics in neurodegenerative diseases resulted from the observations that NRTs such as PBN trap reactive oxygen species and/or secondary free radicals following ischemia. This may occur by converting highly reactive, toxic radicals into much less reactive, much less toxic products. Certain NRTs have been shown to protect experimental animals from ischemia/reperfusion injury (stroke). NRTs, administered chronically, reverse the age-associated increase in oxidatively damaged protein and the age-associated decrease in the activity of the oxidative-sensitive enzyme, glutamine synthetase, in the brain.

Accompanying the NRT-mediated changes in oxidized protein and glutamine synthetase activity is a significant improvement in the performance of animals in behavioral tests measuring short-term spatial memory. It has been shown that prototype NRTs mitigate the effects of this inflammatory cascade in a number of in vivo models. Of particular interest is the consistent and well documented protection shown by PBN against the lethality induced by LPS in various rodent models of septic shock. Remarkably, PBN has also been shown to increase the life span of senescence accelerated mice by one third, perhaps by mitigating free radical damage. PBN has also been shown to block inducible nitric oxide synthetase ("iNOS"), the enzyme responsible for producing large amounts of the highly damaging NO●. Thus, PBN can both trap HO● and suppress formation of NO●, potentially neutralizing the effects of the two agents considered to be the most damaging to tissue.

When evaluating the prospects of using an antioxidant to successfully treat IBD, it is perhaps also useful to consider that the anti-oxidant defense of the human colon is relatively deficient compared to human liver (mucosal levels of SOD, catalase and GSH representing 8%, 4% and 40%, respectively, of liver levels), thus leaving the colon particularly sensitive to oxidative stress.

A considerable number of chemical modifications have been made to increase NRTs suitability as therapeutic agents. The effects of intrinsic chemical reactivity and radical trapping ability have been examined by substituting the phenyl ring with electron donating or electron withdrawing substituents. More water soluble analogues were made by, for example, carboxylate or sodium sulfonate substitution of the phenyl ring. Lipophilic analogues were made with functional group substitutions on either the phenyl ring or the nitronyl nitrogen. The alkyl nitrogen substituent was varied through the standard straight chain and branched $C_3-C_5$ substituents. Nitrone isosteres and related compounds were also targeted and examined for efficacy. This approach lead to various classes of compounds, such as substituted ureas, amides, thioamides, azoxy derivatives, sulphones, and hydroxamic acids.

In addition, some benzamide compounds substantially similar to these nitrones have recently been shown to have activity in the treatment of Parkinson's disease, HIV dementia, and related conditions.

As a final aspect of background, in evaluating the effectiveness of compounds in the treatment of IBD, an in vivo model based upon trinitrobenzene sulfonic acid ("TNBS") is used.

References relating to these subjects include:

Glickman, R M (1994) Inflammatory Bowel Disease in *Harrison's Principles of Internal Medicine* (McGraw Hill, New York, N.Y.) Chapter 255: 1403–1416.

Calkins, B M, Mendeloff, Al (1986) Epidemiology of Inflammatory Bowel Disease, *Epidemiology Review* 8: 60–90.

Levin, B. (1992) Inflammatory Bowel Disease and Colon Cancer, *Cancer (Supplement)*, 70: 1313–1316.

Crotty, B. (1994) Ulcerative Colitis and Xenobiotic Metabolism, *Lancet*, 343: 35–38.

Hanauer, S B, Baert, F. (1994) Medical Therapy of Inflammatory Bowel Disease, *Med Clin North Am*, 78: 1413–1426.

MacDermott, RP (1994) Alterations in the Mucosal System in Ulcerative Colitis and Crohn's Disease, *Med Clin North Am*, 78: 1207–1231.

Hanauer, B. (1993) Medical Therapy of Ulcerative Colitis, *Lancet*, 342: 412–417.

Winrow, V R, Winyard, P G, Morris, C J, Blake, D R (1993) Free radicals in Inflammation: Second Messengers and Mediators of Tissue Destruction, *Br Med Bull* 49: 506–522.

Floyd, R A and Carney, J., Nitrone Radical Traps (NRTs) Protect in Experimental Neurodegenerative Diseases, in *Neuroprotective Approaches to the Treatment of Parkinson's Disease and Other Neurodegenerative Disorders* (Olanow, C W, Jenner, P and Youssim E, Eds.) Academic Press, New York, N.Y., in press.

Cao, X. and Phillis, J W (1994) a-Phenyl-N-tert-butylnitrone Reduces Cortical Infarct and Edema in Rats Subjected to Focal Ischemia. *Brain Res*. 644: 267–272.

Zhao, Q., Pahlmark, K., Smith, M.-J., and Siesjo, B. (1994) Delayed Treatment with the Spin Trap a-phenyln-tert-butyl nitrone (PBN) Reduces Infarct Size Following Transient Middle Cerebral Artery Occlusion in Rats. *Acta Physiol. Scad.* 152: 349–350.

Oliver, C N, Starke-Reed, P E, Stadtman, E R, Carney, J M and Floyd, R A (1990) Oxidative Damage to Brain Proteins, Los of Glutamine Synthetase Activity and Production of Free Radicals During Ischemia Induced Injury to Gerbil Brain. *Proc. Natl. Acad. Sci. USA* 87: 5144–5147.

Carney, J M, Starke-Reed, P E Oliver, C N, Landrum, R W, Cheng, M S, Wu, J F and Floyd, R A (1991) Reversal or age-related increase in brain protein oxidation in enzyme activity, and loss in temporal and spatial memory by chronic administration of the spin-trapping compound N-tert-butyl-α-phenylnitrone. *Proc. Natl. Acad. Sci.*, 88: 3633–3636.

Novelli, G P (1992) Oxygen Radicals in Experimental Shock: Effects of Spin-Trapping Nitrones in Ameliorating Shock Pathophysiology, *Critical Care Medicine*, 20: 499–507.

Hamburger, S A, McCay, P B (1989) Endotoxin-Induced Mortality in Rats is Reduced by Nitrones, *Circulatory Shock*, 29: 329–334.

Progrebniak, H W, Merino, M J, Hahn, S M, Mitchell, J B, Pass, H I (1992) Spin Trap Salvage from Endotoxemia: The Role of Cytokine Down-Regulation, *Surgery*, 112: 130–139.

McKechnie, K., Furman, B L, Paratt J R (1986), Modification by Oxygen Free Radical Scavengers of the Metabolic and Cardiovascular Effects of Endotoxin Infusion in Conscious Rats, *Circulatory Shock* 19: 429–439.

Edamatsu, R, Mori, A., Packer, L (1995) The Spin Trap N-tert-α-phenyl-butylnitrone Prolongs the Life Span of the Senescence Accelerated Mouse, *Biochem Biophys Res Comm* 211: 847–849.

Miyajima, T., Kotake, Y. (1995) Spin Trapping Agent, Phenyl N-Tert_Butyl Nitrone, Inhibits Induction of Nitric Oxide Synthase in Endotoxin-Induced Shock in Mice, *Biochem Biophys Res Commun*, 215: 114–121.

Boettner, G R (1987) ESR Parameters of Spin Adducts, *Free Radical Biology*, 3: 259–303.

Harris, M L, Schiller, H J, Reilly, P M, Donowitz, M, Grisham, M B, Bulkley (1992), Free Radicals and Other Reactive Oxygen Metabolites in Imflammatory Bowel Disease: Cause, Consequence or Epiphenomenom, *Pharmacol. Ther.*, 53: 375–408.

Grisham M B, MacDermott, R P, Deitch E A (1990), Oxidant Defence Mechanisms in the Human Colon, *Inflammation*, 14: 669–680.

Elson, C O, Startor, R B, Tennyson, G S, Ridell, R H (1995), Experimental Models of Inflammatory Bowel Disease, *Gastroenterology*, 109: 1344–1367.

Yamada, T, Marshall, S, Specian, R D, Grisham, M B (1992) A Comparative Analysis of Two Models of Colitis in Rats, *Gastroenterology*, 102: 1524–1534.

Wallace, J A, MacNaughton, W K, Morris, G P, Beck P L (1989) Inhibition of Leulotriene Synthesis Markedly Accelerates Healing in a Rat Model of Inflammatory Bowel Disease, *Gastroenterology*, 95: 29–35.

Higa, A. McKnight, G W, Wallace, J L (1993) Attenuation of Epithelial Injury in Acute Experimental Colitis by Immunomodulators, *Eur. J. Pharmacol.* 239: 171–178.

Castro, G A, Roy, S A, Stockstill, R D (1974) Trichinella Spiralis: Peroxidase Activity in Isolated Cells from the Rat Intestine, *Exp. Parasitol.*, 36: 307–315.

SUMMARY OF THE INVENTION

It has now been found that certain benzamide compounds have activity in the treatment and prophylaxis of IBD.

One aspect of this invention provides a pharmaceutical composition for the treatment of and prophylaxis of inflammatory bowel disease. It involves an effective inflammatory bowel disease-treating amount of a benzamide in a pharmaceutically acceptable carrier.

In preferred aspects, the benzamide is selected from acetamidobenzamides, aminobenzamides and nitrobenzamides, especially materials described by Formula I where R' is a saturated alkyl of from 3 to 5 carbon atoms, each R is independently —NH—CO—CH$_3$, —NO$_2$ or —NH$_2$, and n is 1 or 2. A most preferred benzamide used in this composition is N-tert-butyl-4-acetamidobenzamide (Compound A). These materials and their use in the treatment of Parkinson's disease and related neurological conditions are described in PCT application US/951/04278.

Another aspect of this invention provides a method for treating a patient suffering from or susceptible to an inflammatory bowel condition. This method involves administering to the patient identified as being in need thereof an effective inflammatory bowel condition-treating or prophylaxing amount of a pharmaceutical composition in which a benzamide compound is the active agent. These compositions may be administered orally, parenterally, or rectally. This method is effective where the inflammatory bowel condition is ulcerative colitis or Crohn's disease. Preferred benzamides are as described above.

BRIEF DESCRIPTION OF THE DRAWINGS

This invention will be described with reference being made to the accompanying drawings in which.

DETAILED DESCRIPTION OF THE INVENTION

Benzamides

The treatment of this invention employs one or more benzamides as its active agent. These benzamides include acetamidobenzamides, aminobenzamides and nitrobenzamides such as are described by Formula I. In this formula, R' is a saturated alkyl of from 3 to 5 carbon atoms, each R is independently —NH—CO—$C_{13}$, —$NO_2$ or —$NH_2$, and n is 1 or 2.

FORMULA I

The acetamido, amino or nitro group (or groups) may be located anywhere on the ring. Thus, when n is 1 the acetamido amino or nitro group may be at the 2, 3 or 4 position of the ring; and when n is 2 the acetamido, amino or nitro groups may be at the 2 and 3, 2 and 4, 2 and 5, 2 and 6, 3 and 4, or 3 and 5 positions of the ring. When R' is tert-butyl, R is an acetamido group and n is 1, substitution of the acetamido group in the 3 position is not preferred.

With respect to the alkyl substituents, R', compounds wherein R' is an alkyl which does not have a hydrogen on the alpha carbon, that is, the carbon which bonds to the nitrogen of the ring, are preferred. Examples of these preferred R' groups are tert-butyl and tert-amyl.

Acetamidobenzamides of Formula I of particular interest are:

N-tert-butyl-4-acetamidobenzamide (Compound A);

N-iso-propyl-4-acetamidobenzamide (Compound B);

N-tert-amyl-4-acetamidobenzamide (Compound C); and

N-methylcyclopropyl-4-acetamidobenzamide (Compound E).

N-tert-butyl-4-acetamidobenzamide (Compound A) is the most preferred aetamidobenzamide.

Aminobenzamides and nitrobenzamides of Formula I of particular interest as tive agents are:

N-iso-propyl-4-nitrobenzamide (Compound F);

N-tert-butyl-3-nitrobenzamide (Compound G);

N-tert-butyl-2-nitrobenzamide (Compound H);

N-n-butyl-4-nitrobenzamide (Compound J);

N-n-propyl-4-nitrobenzamide (Compound K);

N-tert-butyl-3, 5-dinitrobenzamide (Compound L);

N-1-methylpropyl-4-nitrobenzamide (Compound M);

N-tert-butyl-4-aminobenzamide (Compound N); and

N-tert-butyl-3-aminobenzamide (Compound P).

N-tert-butyl-4-aminobenzamide (Compound N) is the most preferred of this group of materials.

When the benzamide compound contains an amino group, such as is the case with Compounds N and P, the amine functionality can be present as such or as a salt. In the salt form the amino is protonated to the cation form in combination with a pharmaceutically acceptable anion, such as chloride, bromide, iodide, hydroxyl, nitrate, sulfonate, methane sulfonate, acetate, tartrate, oxalate, succinate, or palmoate. When these aminobenzamides are referred to it is to be understood that these salts are included as well.

Mixtures of two or more of these materials may be employed, if desired.

Pharmaceutical Compositions

The benzamide compound(s) is formulated into pharmaceutical compositions suitable for oral, parenteral (e.g. intravenous or intramuscular injection), or rectal (e.g. suppository) administration.

The compositions for oral administration can take the form of liquid solutions or suspensions, powders, tablets, capsules or the like. In such compositions, the benzamide or its salt is usually a minor component (0.1 to about 50% by weight) with the remainder being various vehicles or carriers and processing aids helpful for forming the desired dosing form. A liquid form may include a suitable aqueous or nonaqueous vehicle with buffers, suspending dispensing agents, colorants, flavors and the like.

A solid form may include, for example, any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, sugar, methyl salicylate, or orange flavoring.

Injectable compositions are commonly based upon injectable sterile saline or phosphate-buffered saline or other injectable carriers known in the art. Again, the active benzamide is typically a minor component, often being from about 0.05 to 10% by weight, with the remainder being the injectable carrier and the like.

Rectal administration is usually by suppository. Suppositories are generally made with a base component of cocoa butter, glycerinated gelatin, hydrogenated vegetable oils, mixtures of polyethylene glycols of various molecular weights, or fatty acid esters of polyethylene glycol. The active benzamide is usually a minor component, often from about 0.05 to 20% by weight, with the remainder being the base component.

The components for orally administrable, injectable compositions and suppositories are merely representative. Other materials, as well as processing techniques and the like, are set forth in Part 8 of *Remington's Pharmaceutical Sciences*, 17th edition, 1985, Mack Publishing Company, Easton, Pa., which is incorporated by reference.

One can also administer the compounds of the invention in sustained release forms or from sustained release drug delivery systems. A description of representative sustained release materials can be found in the incorporated materials in *Remington's Pharmaceutical Sciences*.

Conditions Treated and Treatment Regimens

The conditions treated with the benzamide-containing compositions generally include IBD and the various symptoms which fall within a definition of IBD. The benzamide-containing formulations can be administered to achieve a therapeutic effect. The benzamide compounds exhibit a long residency in the body. This suggests that a convenient, once-a-day regimen is possible. Other results indicate that multiple doses, such as up to three doses per day, typically, can possible offer more effective therapy. Thus, a single dose or a multidose regimen may be used.

The benzamide-containing composition is administered in manners designed to get the drug into the patient's bloodstream. One excellent mode for accomplishing this is intravenous administration. Intravenous dose levels for treating IBD range from about 0.01 mg/kg/hour of active benzamide to about 100 mg/kg/hour, all for from about 1 to about 120 hours and especially 1 to 96 hours. A preloading bolus of from about 50 to about 5000 mg may also be administered to achieve adequate steady state levels. Other forms of parenteral administration, such as intramuscular injection can be used, as well. In this case, similar dose levels are employed.

With oral dosing, one to three oral doses per day, each from about 0.1 to about 150 mg/kg of active benzamide are called for with preferred doses being from about 0.15 to about 100 mg/kg.

With rectal dosing, one to three rectal doses per day, each from about 1 to about 150 mg/kg of active benzamide are called for with preferred doses being from about 1 to about 100 mg/kg.

In any treatment regimen, the health care professional should assess the patient's condition and determine whether or not the patient would benefit from benzamide treatment. Some degree of experimentation to determine an optimal doing level and pattern may be needed.

A positive dose-response relationship has been observed. As such and bearing in mind the severity of the side effects and the advantages of providing maximum possible amelioration of symptoms, it may be desired in some settings to administer large amounts of benzamide such as those described above.

Methods of Preparation of Compounds

The benzamide compounds employed herein can be prepared using commonly available starting materials and readily achievable reactions. One representative preparation route, which is illustrated with tert-butyl amine, but which may be used with any alkyl amine, involves the following reactions:

(A)

here X is halo such as I, Br, F or Cl.

(B)

(C)

In step (A) the N-tert-butyl nitrobenzamides (III) are formed. This reaction should be carried out at temperatures below 10° C.

This step (A) yields as benzamides III, the compounds of the invention where R is —$NO_2$.

In step (B) the nitro groups in the mono- or di-nitro benzamide III are subjected to reduction. This is commonly carried out with a reducing agent such as hydrazine and an appropriate catalyst such as a heterogeneous platinum, iron oxide hydroxide, palladium or nickel catalyst, typically on a support, or with hydrogen gas and a catalyst.

This step (B) yields as benzamides IV, the compounds of the invention where is $NH_2$.

In step (C) the amino-benzamides IV are converted to acetamidobenzamides V by reaction with an acetyl halide such as acetylchloride. This reaction is carried out in the presence of a mild base and at low to ambient temperatures such as −20° C. to +20° C. This yields the compounds of the invention where R is acetamido.

Alternate synthetic schemes may also be used to prepare the compounds. Examples of these alternate routes are set forth below using Compound A as the representative compound. Other compounds may be prepared using these alternate methods by starting with appropriate starting materials, such as 2- or 3- amino- or nitro-benzonitrile or 2,3-, 2,4-, 2,5-, 2,6-, 3,4- or 3,5- diamino- or dinitro-benzonitrile and the appropriate alcohol (Alternate Route 1) or similarly substituted toluene compounds and the appropriate alkyl amine (Alternate Route 3).

Alternate Route 1

This route begins with acetylation of, for example, 4-aminobenzonitrile (A) to compound (B) using standard methods. Acid hydrolysis of tert-butanol in the presence of 4-acetamidobenzonitrile (B), provides a feasible synthetic pathway to Compound A.

11
-continued

C

Alternate Route 2

Acetylation, using standard methods, of the inexpensive starting material PABA (C) affords a cheap method to produce 4-acetamidobenzoic acid (D). Conversion of (D) to the acid chloride (E) using standard methods (e.g., $SOCl_2$) and subsequent amidation using standard methods, such as those described previously, produces Compound A from inexpensive raw materials.

Alternate Route 3

Another method for the preparation of the compounds begins with acetylation, using standard methods, of, for example, paratoluidine (F) to 4-acetamidotoluene (G). The synthetic intermediate (G) may be converted to 4-acetamidobenzoic acid (D) with common oxidizing agents (e.g., $KMnO_4$) and subsequently transformed to Compound A as outlined in Alternate Route 2.

EXAMPLES

The invention will be further described by the following Examples. These are provided to illustrate several preferred embodiments of the invention but are not to be construed as limiting its scope which is, instead, defined by the appended claims. Examples 1 to 19 demonstrate the preparation of acetamidobenzamides, as well as nitro- and aminobenzamides, which are representative of the benzamide compounds employed in the compositions and methods of this invention. Examples 20 to 24 demonstrate the preparation of pharmaceutical compositions based on the compounds. Thereafter biological test results illustrating the activity of the compositions of the invention are provided.

Example 1

Preparation of N-tert-Butyl-4-aminobenzamide (Compound N)

tert-Butyl amine (14.6 g, 0.200 mole) was stirred in ethyl acetate (150 mL, purified by washing with 5% sodium carbonate solution, saturated sodium chloride solution, drying over anhydrous magnesium sulfate, and filtering through fluted filter paper) and cooled to 5° C. with an ice bath. 4-nitrobenzoyl chloride (18.6 g, 0.100 mole) in purified ethyl acetate (75 mL) was added dropwise at such a rate to maintain the temperature below 10° C. The ice bath was removed upon complete addition of benzoyl chloride solution and the reaction stirred for 4 hours. The reaction mixture was then filtered on a Buichner funnel, the filtrate washed three times with 5% HCl, once with saturated sodium chloride, dried over anhydrous magnesium sulfate, filtered through fluted filter paper, and the solvent stripped off leaving white crystalline product. The product was dried in a vacuum oven at 24 mm and 45° C. for 14 hours. This procedure produced 17.13 g of crystals of N-tert-butyl-4-nitrobenzamide (Compound Q) (77% yield), mp 162-163° C. Proton nuclear magnetic resonance (89.55 MHz in $CDCl_3$) showed absorptions at 8.257 ppm (d, 8.8 Hz, 2H; 3,5-aryl H); 7.878 ppm (d, 8.8 Hz, 2H; 2,6-aryl H); 6.097 ppm (bs, 1H; N—H); 1.500 ppm (s, 9H; ter-butyl H).

Palladium on carbon (5%, 75 mg) was added to Compound Q (5 g, 22.5 mmole) in 95% ethanol at 55° C. A solution of hydrazine (1.2 mL) in 95% ethanol (10 mL) was added dropwise over 30 min. and more Pd/C added (75 mg). The reaction was refluxed 3 hours, hydrazine (0.5 g) in 95% ethanol (5 mL) was added and the reaction was refluxed for another hour. The reaction was filtered on a Büchner funnel, the volume of solvent reduced under vacuum, and extracted with dichloromethane. The combined extracts were dried over magnesium sulfate and solvent stripped, leaving 3.90 g of N-tert-butyl-4-aminobenzamide (Compound N) (90% yield), melting point 125–127 ° C. 90 MHz proton NMR (in $CDCl_3$) showed absorbances at 7.290 ppm (2H, d, 8.8 Hz; 2,6 aryl H); 6.368 ppm (2H, d, 8.8 Hz; 3,5 aryl H); 5.45 ppm (1 H, bs; NHC=O); 3.727 ppm (2H, bs; aryl-$NH^2$); 1.186 ppm (9 H, s; t-butyl H).

Example 2

Preparation of N-tert-Butyl-4-acetamidobenzamide (Compound A)

Acetyl chloride (0.45 g, 5.7 mmole) in ethyl acetate (25 mL) was added dropwise to Compound N (1.0 g, 5.2 mmole) and triethyl amine (0.58 g, 5.7 mmole) in ethyl acetate at 3° C. at such a rate to maintain the temperature below 10° C. The reaction was allowed to warm to room temperature, stirred 1 hour, and washed with 5% HCl. Recrystallization from acetone gave 1.08 g N-tert-butyl-4-acetamidobenzamide (Compound A)(89% yield), melting point 119–121 ° C. 90 MHz proton NMR (in DMSO-d6) showed absorbances at 9.726 ppm (1H, bs, N—H); 7.715 ppm (4H, dd, 4.4 Hz; aryl H); 7.295 ppm (1 H, bs; NH); 2.844 ppm (3H, s; $CH_3CO$); 1.448 ppm (9 H, s; t-butyl H).

Example 3

Preparation of N-tert-Butyl-3-nitrobenzamide (Compound G) N-tert-butyl-3-aminobenzamide (Compound P) and N-tert-butyl-3-acetamidobenzamide (Compound D)

The amidation procedures of Example 1 were followed using 3-nitrobenzoyl chloride instead of 4-nitrobenzoyl chloride. This gave N-tert-butyl-3-nitrobenzamide (Compound G) in 92% yield, melting point 123–125 ° C. Proton NMR (in $CDCl_3$) showed absorptions at 8.517 ppm (2-aryl H, s, IH); 8.337 ppm (4-aryl H, d, 8.8 Hz, 1H); 8.121 ppm (6-aryl H, d, 6.4 Hz, 1H); 7.618 ppm (5-aryl H, m, 1H); 6.032 ppm (N—H, bs, 1H); 1.484 ppm (t-butyl H, s, 9 H).

Iron (III) oxide hydroxide catalyzed hydrazine reduction produced N-tert-butyl-3-aminobenzamide (Compound P) in 53% yield, melting point 118–120 ° C. Proton NMR (in $CDCl_3$) showed absorbances at 7.088 ppm (4–6 -aryl H, m, 3 H); 6.794 ppm (2-aryl H, s, 1H); 5.902 ppm (N-H, bs, 1H); 3.145 ppm (aryl N-H, bs, 2H); 1.458 ppm (t-butyl H, s, 9 H).

Acetylation of Compound P as described in Example 2 gave N-tert-butyl-3-acetamidobenzamide (Compound D) in 75% yield, melting point 194–195° C.

Proton NMR (in $CDCl_3$) showed absorptions at 7.778 ppm (4–6 -aryl H, m, 3 H); 7.392 ppm (2-aryl H, s, 1H); 6.08 ppm (N—H, bs, 1H); 2.174 ppm (acetyl $CH_3$, s, 9 H); 1.500 ppm (t-butyl H, s, 9 H).

Example 4

Preparation of N-tert-butyl-2-nitrobenzamide (Compound H) and N-tert-butyl-2-acetamidobenzamide The method of Example 3 is repeated using 2-nitrobenzoyl chloride in the amidation step. This yields N-tert-butyl-2-nitrobenzamide (Compound H).

Reduction of the nitrobenzamide with hydrazine yields N-tert-butyl-2-aminobenzamide.

Acetylation of the aminobenzamide yields N-tert-butyl-2-acetamidobenzamide.

Example 5

Preparation of N-iso-propyl-4-nitrobenzamide (Compound F) and N-iso-propyl-4-acetamidobenzamide (Compound B)

The method of Example 3 is repeated using 4-nitrobenzoyl chloride and iso-propyl amine in the amidation step. This yields N-iso-propyl-4-nitrobenzamide (Compound F).

Reduction of the nitrobenzamide with hydrazine yields N-iso-propyl-4-aminobenzamide.

Acetylation of the aminobenzamide yields N-iso-propyl-4-acetamidobenzamide (Compound B).

Example 6

Preparation of N-tert-amyl-4-nitrobenzamide and N-tert-amyl-4-acetamidobenzamide (Compound C)

The method of Example 3 is repeated using 4-nitrobenzoyl chloride and tert-amyl amine in the amidation step. This yields N-tert-amyl-4-nitrobenzamide.

Reduction of the nitrobenzamide with hydrazine yields N-tert-amyl-4-aminobenzamide.

Acetylation of the aminobenzamide yields N-tert-amyl-4-acetamidobenzamide (Compound C).

Example 7

Preparation of N-iso-butyl-4-acetamidobenzamide

The method of Example 3 is repeated using 4-nitrobenzoyl chloride and iso-butyl amine in the amidation step. This yields N-iso-butyl-4-nitrobenzamide.

Reduction of the nitrobenzamide with hydrazine yields N-iso-butyl-4-aminobenzamide.

Acetylation of the aminobenzamide yields N-iso-butyl-4-acetamidobenzamide.

Example 8

Preparation of N-n-butyl-4-nitrobenzamide (Compound J) and N-n-butyl-4-acetamidobenzamide The method of Example 3 is repeated using 4-nitrobenzoyl chloride and n-butyl amine in the amidation step. This yields N-n-butyl-4-nitrobenzamide (Compound J).

Reduction of the nitrobenzamide with hydrazine yields N-n-butyl4-aminobenzamide.

Acetylation of the aminobenzamide yields N-n-butyl-4-acetamidobenzamide.

Example 9

Preparation of N-n-propyl-4-nitrobenzamide (Compound K) and N-n-propyl-4-acetamidobenzamide The method of Example 3 is repeated using 4-nitrobenzoyl chloride and n-propyl amine in the amidation step. This yields N-n-propyl-4-nitrobenzamide (Compound K).

Reduction of the nitrobenzamide with hydrazine yields N-n-propyl-4-aminobenzamide.

Acetylation of the aminobenzamide yields N-n-propyl-4-acetamidobenzamide.

Example 10

Preparation of N-1,2-dimethylpropyl-4-nitrobenzamide and N-, 2-dimethylpropyl-4-acetamidobenzamide The method of Example 3 is repeated using 4-nitrobenzoyl chloride and 1,2-dimethylpropyl amine in the amidation step. This yields N-1,2-dimethylpropyl-4-nitrobenzamide.

Reduction of the nitrobenzamide with hydrazine yields N-1,2-dimethylpropyl-4-aminobenzamide.

Acetylation of the aminobenzamide yields N-1,2-dimethylpropyl-4-acetamidobenzamide.

Example 11

Preparation of N-n-pentyl-4-nitrobenzamide and N-n-pentyl-4-acetamidobenzamide

The method of Example 3 is repeated using 4-nitrobenzoyl chloride and n-pentyl amine in the amidation step. This yields N-n-pentyl-4-nitrobenzamide.

Reduction of the nitrobenzamide with hydrazine yields N-n-pentyl-4-aminobenzamide.

Acetylation of the aminobenzamide yields N-n-pentyl-4-acetamidobenzamide.

Example 12

Preparation of N-2-methylbutyl-4-nitrobenzamide and N-2-methylbutyl-4-acetamidobenzamide The method of Example 3 is repeated using 4-nitrobenzoyl chloride and 2-methylbutyl amine in the amidation step. This yields N-2-methylbutyl-4-nitrobenzamide.

Reduction of the nitrobenzamide with hydrazine yields N-2-methylbutyl-4-aminobenzamide.

Acetylation of the aminobenzamide yields N-2-methylbutyl-4-acetamidobenzamide.

Example 13

Preparation of N-n-pentyl-2-nitrobenzamide and N-n-pentyl-2-acetamidobenzamide The method of Example 3 is repeated using 2-nitrobenzoyl chloride and n-pentyl amine in the amidation step. This yields N-n-pentyl-2-nitrobenzamide. Reduction of the nitrobenzamide with hydrazine yields N-n-pentyl-2-aminobenzamide.

Acetylation of the aminobenzamide yields N-n-pentyl-2-acetamidobenzamide.

Example 14

Preparation of N-tert-butyl-2,3-diacetamidobenzamide

The method of Example 3 is repeated using 2,3-dinitrobenzoyl chloride in the amidation step. This yields N-tert-butyl-2,3-dinitrobenzamide.

Reduction of the nitrobenzamide with hydrazine yields N-tert-butyl-2,3-diaminobenzamide.

Acetylation of the aminobenzamide yields N-tert-butyl-2,3-diacetamidobenzamide.

Example 15

Preparation of N-tert-amyl-2,4-diacetamidobenzamide

The method of Example 3 is repeated using 2,4-dinitrobenzoyl chloride and tert-amyl amine in the amidation step. This yields N-tert-amyl-2,4-dinitrobenzamide.

Reduction of the nitrobenzamide with hydrazine yields N-tert-amyl-2,4-diaminobenzamide.

Acetylation of the aminobenzamide yields N-tert-amyl-2,4-diacetamidobenzamide.

Example 16

Preparation of N-tert-butyl-2,5-diacetamidobenzamide

The method of Example 3 is repeated using 2,5-dinitrobenzoyl chloride in the amidation step. This yields N-tert-butyl-2,5-dinitrobenzamide.

Reduction of the nitrobenzamide with hydrazine yields N-tert-butyl-2,5-diaminobenzamide.

Acetylation of the aminobenzamide yields N-tert-butyl-2,5-diacetamidobenzamide.

Example 17

Preparation of N-tert-butyl-2,6-diacetamidobenzamide

The method of Example 3 is repeated using 2,6-dinitrobenzoyl chloride in the midation step. This yields N-tert-butyl-2,6-dinitrobenzamide.

Reduction of the nitrobenzamide with hydrazine yields N-tert-butyl-2,6-diaminobenzamide.

Acetylation of the aminobenzamide yields N-tert-butyl-2,6-diacetamidobenzamide.

Example 18

Preparation of N-tert-butyl-3,4-diacetamidobenzamide

The method of Example 3 is repeated using 3,4-dinitrobenzoyl chloride in the amidation step. This yields N-tert-butyl-3,4-dinitrobenzamide.

Reduction of the nitrobenzamide with hydrazine yields N-tert-butyl-3,4-diaminobenzamide.

Acetylation of the aminobenzamide yields N-tert-butyl-3,4-diacetamidobenzamide.

Example 19

Preparation of N-tert-butyl-3,5-diacetamidobenzamide

The method of Example 3 is repeated using 3,5-dinitrobenzoyl chloride in the amidation step. This yields N-tert-butyl-3,5-dinitrobenzamide.

Reduction of the nitrobenzamide with hydrazine yields N-tert-butyl-3,5-diaminobenzamide.

Acetylation of the aminobenzamide yields N-tert-butyl-3,5-diacetamidobenzamide.

Preparation of Pharmaceutical Compositions:

Example 20

The compound of Example 1 is admixed as a dry powder with a dry gelatin binder in an approximate 1:2 weight ratio. A minor amount of magnesium stearate is added as a lubricant. The mixture is formed into 240–270 mg tablets (80–90 mg of active benzamide) in a tablet press. Administration of these tablets on a daily, twice daily or thrice daily regimen to a patient suffering from IBD would treat the patient's disease.

Example 21

The compound of Example 2 is admixed as a dry powder with a starch diluent in an approximate 1:1 weight ratio. The mixture is filled into 250 mg capsules (125 mg of active benzamide). Administration of these capsules on a daily, twice daily or thrice daily regimen to a patient suffering from IBD would treat the patient's disease.

Example 22

The compound of Example 3 is suspended in a sweetened flavored aqueous medium to a concentration of approximately 50 mg/mL. Administration of 5 mLs of this liquid on a daily, twice daily or thrice daily regimen to a patient suffering from IBD would treat the patient's disease.

Example 23

The compound of Example 4 is admixed as a dry powder with a dry gelatin binder in an approximate 1:2 weight ratio. A minor amount of magnesium stearate is added as a lubricant. The mixture is formed into 450–900 mg tablets (150–300 mg of active benzamide) in a tablet press. Administration of these tablets on a daily, twice daily or thrice daily regimen to a patient suffering from IBD would treat the patient's disease.

Example 24

The compound of Example 14 is dissolved in a buffered sterile saline injectable aqueous medium to a concentration of approximately 5 mg/ml. If 50 mLs of this liquid material were administered on a daily, twice daily or thrice daily regimen to a patient with IBD, this dose would alleviate the symptoms of the disease.

It will be appreciated that any of the compounds of Formula I could be employed in any of these representative formulations, and that any of these formulations could be administered in any of these manners so as to treat any IBD conditions described in this specification.

Biological Experiments

Compounds of the invention were tested for IBD-treating activity as will be detailed below.

One group of tests looked at phamacokinetic issues such as clearance rate. Another group of tests looked at efficacy in animal models for IBD. From these experiments, Compounds A and N were determined to show the most promise.

Pharmacokinetic Studies

Bioavailability of Compounds A and N

The absolute oral bioavailability of Compound A was determined by comparing the area-under-the-curve ("AUC") following a 20 mg/kg IV dose of Compound A (2 ml/kg, 75% PEG solution) to a 20 mg/kg dose of Compound A dissolved in 1% methyl cellulose. Blood concentrations were determined at 0, 0.083, 0.15, 0.5, 1, 2, 4, 8, and 24 hours post-IV dose and 0, 0.5, 1, 2, 4 and 8 hours post-oral dose. Four animals were dosed orally and four animals were dosed intravenously.

The blood samples were analyzed by HPLC. Detection was by UV at 262 nm. Responses were converted to concentrations by comparison to responses from calibration standards injected onto the column. The resulting concentrations were used to calculate the AUC. Through oral dosing, there was an absolute bioavailability of 52% of Compound A.

In another experiment, six rats were orally dosed with 30 mg/kg of Compound A dissolved in 1% methyl cellulose. Blood samples were taken at 0.5, 1, 2, 5, 8, 12, 16, 20 and 24 hours. The apparent $t_{1/2}$ for Compound A in the blood was 8 hours. This is a very long $t_{1/2}$ for a drug in rats and is a good predictor of once-a-day dosing for Compound A in humans. Such a dosing regimen would be a significant therapeutic advantage in the clinic.

Figure 10:
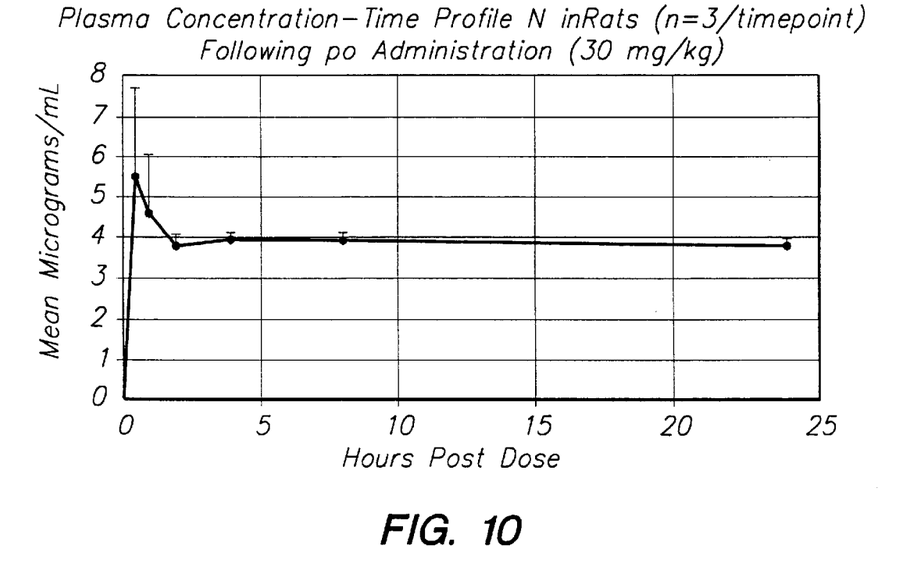
FIG. 10 is a graph showing plasma concentration of Compound N as a function of time.

An additional series of bioavailability experiments were conducted using compounds A and N. These studies confirmed the excellent bioavailability of compound A and demonstrated similar results for compound N. The results are given in Table 1. The bioavailability of compound N is depicted in FIG. 10 as well.

TABLE 1

PK Parameter Estimates for Most Active NRTs from Screening
(NRTs Dosed 30 mg/kg po in 1% Methyl Cellulose, n = 3 rats/NRT)

| Compound | A | N |
| --- | --- | --- |
| $C_{max}$ (μg/mL) | 34 | 5.4 |
| $T_{max}$ (h) | 8.0 | 0.5 |
| $AUC_{0-\infty}$ (μg · hr/mL) | 745 | 1026 |
| Elim · t½ (h) | 11 | 355 |

As FIG. 10 shows, for Compound N, $T_{max}$ occurs early at 0.5 h, and, although $C_{max}$ is somewhat lower than that found following dosing with Compound A, the lower clearance of Compound N results in an overall greater systemic exposure for a given dose for Compound N than for Compound A. In addition, the extremely long terminal half-life observed for Compound N may partially explain the extraordinary efficacy of the compound because the half-life permits the presence of Compound N following a single dose at a substantial concentration throughout the complete multi-day inflammatory process. The exceptionally long $t_{1/2}$ of Compound N in rats predicts possibly weekly dosing with Compound N. In this regard, note the relatively low variability in plasma concentration of Compound N once the absorption and initial elimination phase are complete.

Efficacy Studies

TNBS Model

The trinitrobenzene sulphonic acid ("TNBS") model is one of the standard IBD models used in IBD discovery research, and has been extensively evaluated in rodents. A single enema of TNBS induces a prolonged colonic inflammatory response (up to several weeks) that is transmural and is accompanied by oxidative damage as evidenced by an increase in myeloperoxidase ("MPO") activity. Furthermore, the inflammation is characterized by discrete areas of acute necrosis, inflammation and muscle thickening. Agents with anti-inflammatory effects in patients with IBD show efficacy in this model. Although the mechanism by which TNBS induces an inflammatory response is unknown, it is thought to have an immunological basis.

Induction of Colitis

Male Sprague-Dawley rats (200–250 g) were housed in standard cages (2 per cage) and fed rat chow and tap water ad libitum. After an overnight fast, rats were brought into the laboratory and randomized into treatment groups. Colitis was induced by intrarectal administration of 0.5 ml of TNBS solution (50 mg/kg in 50% ethanol) using a 1 ml syringe attached to a 5 cm polyethylene catheter. Control animals received saline (0.9%) or a 1 % methyl cellulose suspension at identical time points.

Tissue Analysis

Three days after TNBS administration, the rats were sacrificed and the colons excised and opened longitudinally. In 5 cm segments of colon, gross morphology was determined using the scale given in Table 2:

TABLE 2

TNBS Morphology Grading Standards

| Grade | Finding |
| --- | --- |
| 0 | No damage |
| 1 | One area of Inflammation (red), no ulcers |
| 2 | Ulcers, no area of inflammation |
| 3 | Ulcers, one area of inflammation |
| 4 | More than 2 ulcers, inflammation at one site |
| 5 | More than 2 ulcers, inflammation > 1 cm |

The weights of each 5 cm colonic segment were also recorded to assess inflammatory induced edema.

MPO Activity

Myeloperoxidase ("MPO") activity is measured as an index of the intensity of the inflammatory response. In order to determine the MPO activity, a blind study of 300 mg samples of colon tissue were analyzed. This assay uses the spectrophotometric method of Castro et al.

Dosing Regimen

For PO (oral) dosing, Compound A was administered by oral gavage 30 mg/kg as a 1% carboxy methyl cellulose ("CMC") suspension 1 hour prior to the administration of TNBS. Control rats were given CMC only. For IV (intravenous) dosing, Compound A was administered 30 mg/kg by tail vein injection in a 75% PEG/25 % water solution 1 hour prior to administration of TNBS. Control rats were given an injection of 75% PEG/25 % water only. Six rats were dosed for each route of administration.

Figure 1:
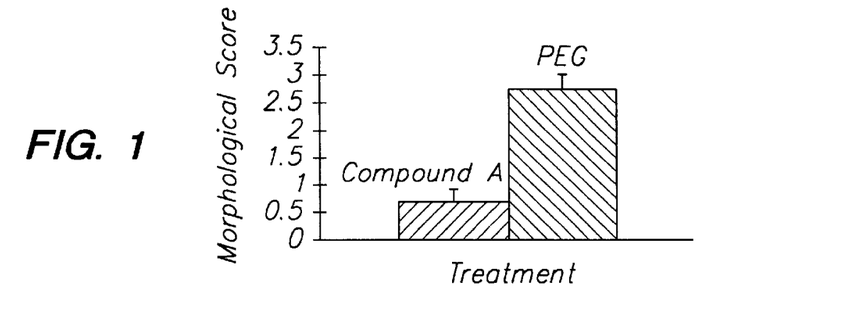
FIG. 1 is a comparison of morphological scores seen with treatment with PEG alone (used as a control) and Compound A on colon tissue where IBD was induced with trinitrobenzene sulphonic acid ("TNBS")
Figure 2:
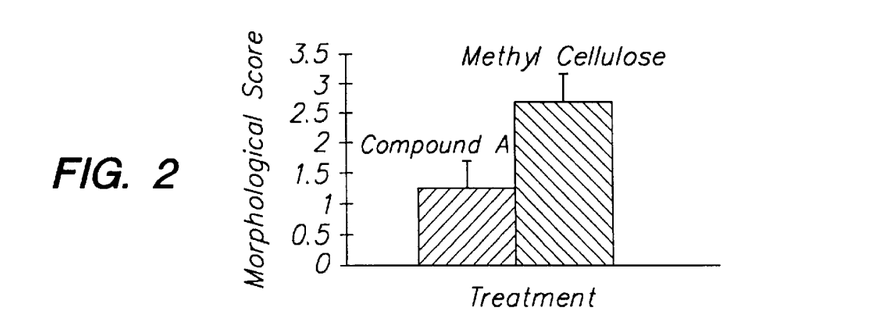
FIG. 2 is a comparison of morphological scores seen with treatment with methyl cellulose (used as a control) and Compound A on colon tissue where IBD was induced with TNBS.
Figure 3:
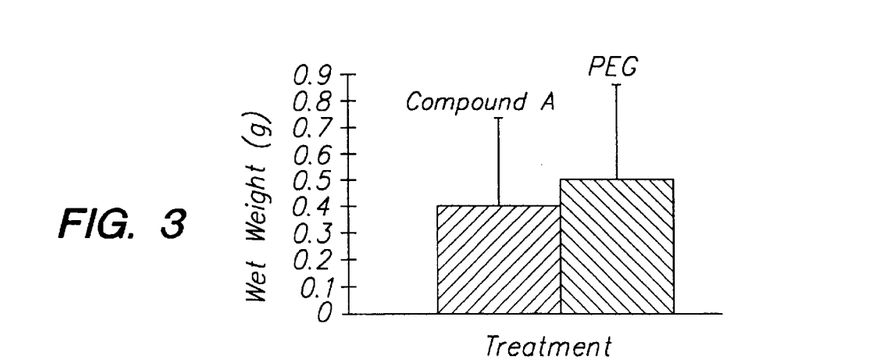
FIG. 3 is a comparison of the effect on colon tissue weight when treated with PEG alone (used as a control) and Compound A.
Figure 4:
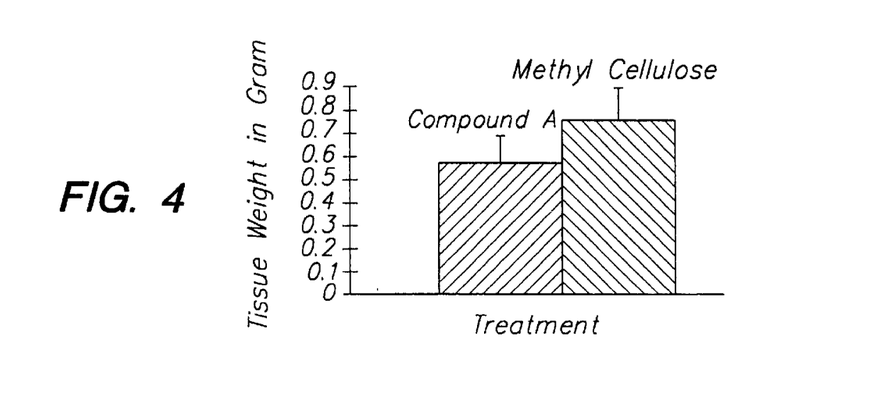
FIG. 4 is a comparison of the effect on colonic tissue weight of administration of 30 mg/kg Compound A and methyl cellulose alone (control) in the TNBS/IBD model in rats.
Figure 5:
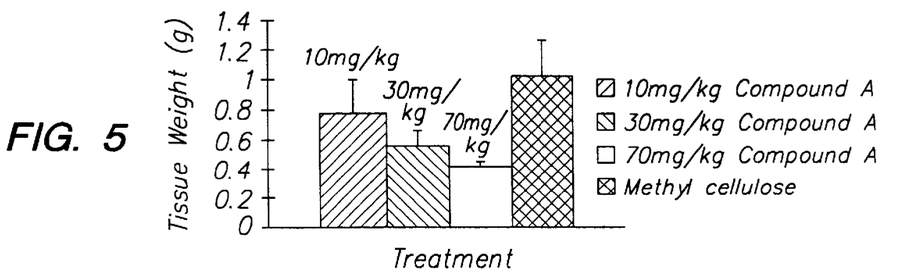
FIG. 5 is a comparison of the effect on colonic tissue weight with varying doses of Compound A and methyl cellulose (control)
Figure 6:
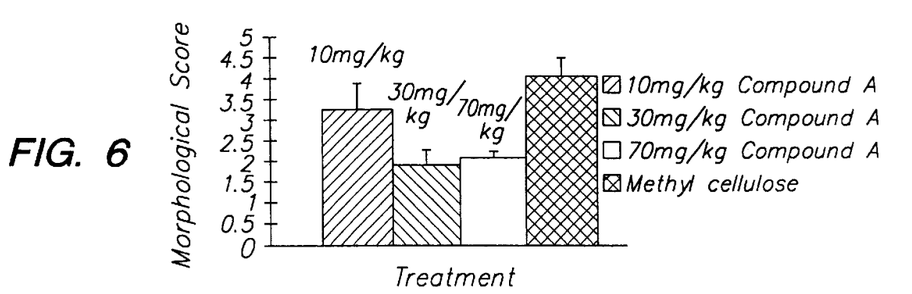
FIG. 6 is a comparison of morphological scores with varying doses of Compound A and methyl cellulose (control).

An additional study was conducted varying the amount of Compound A administered to the rats. Doses of 10 mg/kg, 30mg/kg, and 70 mg/kg were given by oral administration.
Results of TNBS Studies
Both IV and Oral Dosing are Effective Tissue analysis and morphological scores were calculated for both the IV and PO dosing. FIGS. 1 and 3 show that intravenous treatment with Compound A decreases the severity of IBD symptoms. FIGS. 2 and 4 show that oral dosing with Compound A also decrease the severity of IBD symptoms. FIGS. 5 and 6 illustrate the effect on tissue weight and morphological score when the dosage of Compound A was varied.

Based on gross tissue morphology measurements, both the IV and PO administration of Compound A protected from the damage induced by TNBS. The greater protection seen following IV administration is consistent with both the 50% bioavailability of Compound A in rats and the idea that the compound is working systemically and not just topically.

MPO activity measurements were performed only for samples from the IV administration. The results in Table 3 below suggest that Compound A provided protection from the TNBS insult.

TABLE 3

Intravenous Treatment with Compound A Protects in the TNBS Model of IBD as Measured by Myeloperoxidase Activity

| Treatment (IV) | MPO Activity (units/mg) |
| --- | --- |
| Vehicle (CMC control) | 2.88 ± 0.72 |
| Compound A | 1.77 ± 0.53 |

Figure 7:
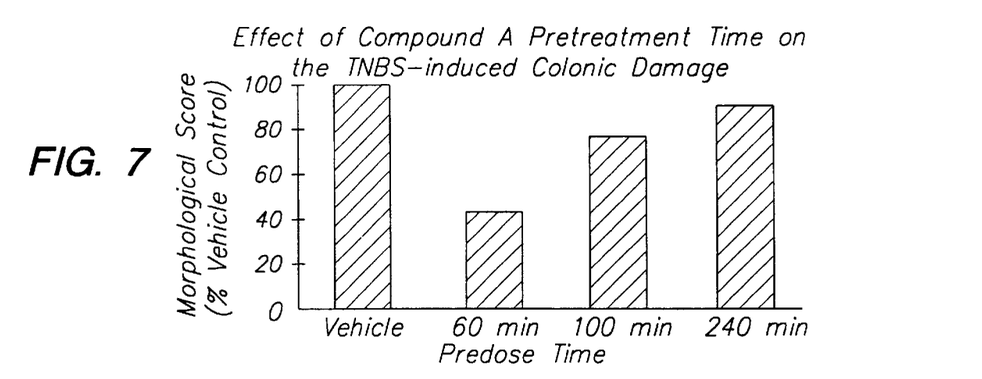
FIG. 7 is a comparison of morphological scores with varying times of dosing with Compound A.

Tissue weight results are shown in FIGS. 3 and 4, and suggest protection, but not as convincingly as the morphology and MPO activity results.
The Treatment Exhibits a Dose-Response Relationship A more detailed dose-response investigation of the protective effects of Compound A administered orally in the rat model of IBD (FIGS. 5 and 6) showed that the compound possesses minimal protective effects at 10 mg/kg, increased protective effects at 30 mg/kg, and 70 mg/kg showing the strongest protective effect.
Protection is Time-Dependent A study was run to determine whether or not the effectiveness of Compound A was dependent upon when it was administered relative to the TNBS administration. As shown in FIG. 7, the prevention the inflammatory degeneration was dependent on the time of Compound A administration relative to TNBS treatment. The best protection was obtained when Compound A was administered 1 hour before TNBS. With a pretreatment interval of 120 mins between the Compound A (30 mg/kg po) and the TNBS enema, we continued to observe a protective effect against the TNBS-induced colonic inflammation, although it was less protective compared to the 60 min pretreatment period. The effect of a single dose of Compound A administered 240 mins prior to TNBS appeared to show little protection against morphological changes induced by the insult. These results indicate protection against TNBS induced inflammatory colitis in the rat when administered prior to TNBS treatment.

These results establish that the 1 hour time point provides greater protection than the two hour time point. The reason for the time-dependency is not totally clear but it may be that it reflects a combined effect of the kinetics of Compound A and the cascade of events that leads to TNBS-induced inflammation.

As will be described below, our studies show that, following oral administration, plasma concentrations of Compound A peak around 3–4 hours and begin to decline after 7 hours. Under the experimental conditions studied here, events that occur more that 6 hours after TNBS administration would encounter very different concentrations of Compound A. For example at the time point Compound A administered 1 hour before would still be at its peak whereas in animals that received Compound A, 4 hours before TNBS would have levels approximately 30% lower. Although it might seem that a direct interaction between Compound A and TNBS in the colon could also explain these results this is unlikely since intravenous administration of Compound A also provides protection. Thus, these findings indicate that Compound A protects against TNBS-induced colitis by altering one or more specific components of the inflammatory cascade.
Multiple Doses are Effective The results above suggest that levels of Compound A need to remain elevated for some hours after TNBS treatment in order to prevent inflammatory damage. As a follow-on set of experiments we investigated the effects of multiple doses of Compound A administered after TNBS treatment.

Experimental conditions were similar to those described above except that rats were given either Compound A (30 mg/kg PO) or vehicle, administered 4, 8 and 24 hours after TNBS treatment for at total of 3 doses.

Figure 8:
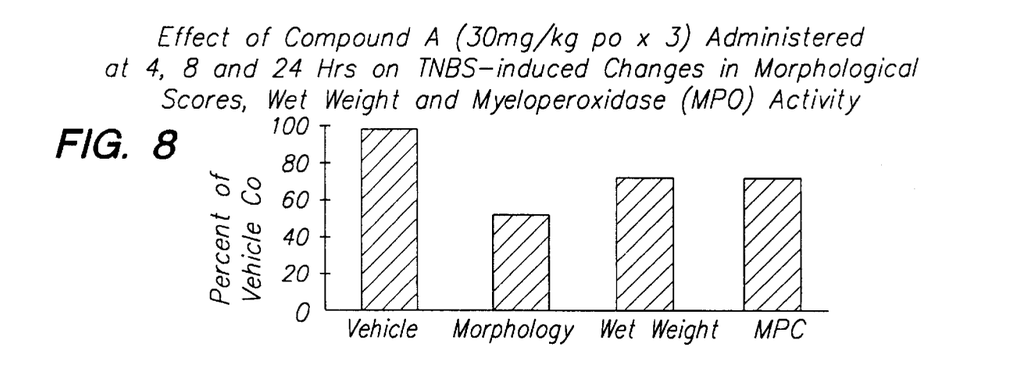
FIG. 8 is an illustration of the effectiveness of a three dose regimen of Compound A.
Figure 9:
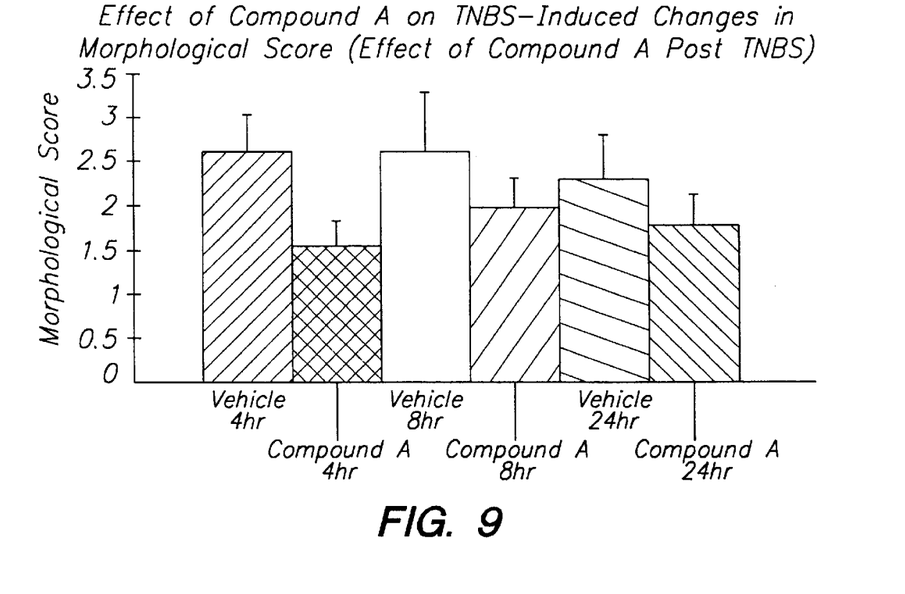
FIG. 9 is an illustration of the effect of Compound A when administered repeatedly with repeated intervening TNBS challenges.

Under this experimental design, we found, that in vehicle-treated rats, the TNBS enema produced distal colon damage, stimulated colonic MPO levels and increased the weight of the colonic segments. In Compound A treated animals TNBS-induced colonic tissue damage was significantly reduced. Furthermore, these finds were confirmed biochemically, through a decrease in MPO activity and a reduction in tissue wet weight (FIG. 8). The results of these studies support the hypothesis that Compound A prevention of TNBS-induced damage occurs some hours after colonic insult, and is dependent on high plasma concentrations at time points after the insult. These findings also show that Compound A not only protects colonic tissue against inflammatory damage but that the drug can actually interrupt or intervene in the inflammatory process even after it has been initiated. The observation of such anti-inflammatory activity suggests that the clinical potential of NRTs includes both prophylaxis as well as treatment of active inflammation.

In another series of experiments to investigate the duration of action of Compound A was designed to advance previous observations and determine whether a single dose of 90 mg/kg po Compound A given either 4, 8, or 24 hrs after the TNBS enema would reduce the colonic damage.

Experimental conditions were similar to those described above except that rats were given a single large dose of Compound A (90 mg/kg PO) or vehicle either 4, 8 or 24 hours after TNBS treatment.

The results of these experiments demonstrate that a single dose of Compound A (90 mg/kg po) given after the TNBS enema prevents inflammatory damage. However, a single dose possessed less efficacy than the 3 dose (30 mg/kg) oral regimen (FIG. 8).

In summary, these tests show that Compound A exhibits good activity in protecting colon tissue from damage caused by a toxin commonly used to induce a colitis which mimics IBD. The protection occurs when Compound A is administered either IV or PO. Protection has been demonstrated in morphology, MPO activity and tissue weight measurements at a reasonably low dose.

Evaluation of the dose-response characteristics of Compound A in the TNBS model

The objective of this series of experiments was to determine the dose-response curve for Compound A in the TNBS model and evaluate basic pharmacological parameters ($ED_{50}$, $E_{max}$).

Groups of rats (N=11/group) were administered increasing doses of Compound A (0–90 mg/kg-po) 1 hour prior to TNBS enema. In addition to macroscopic assessment, the wet weight of the tissue was also measured as an additional secondary efficacy parameter.

Figure 11:
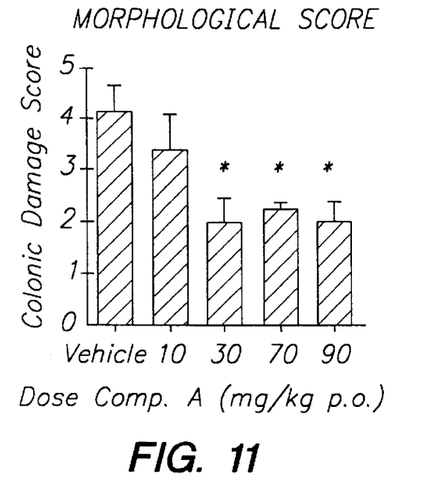
FIG. 11 shows morphological scores as a function of Compound A dose.
Figure 12:
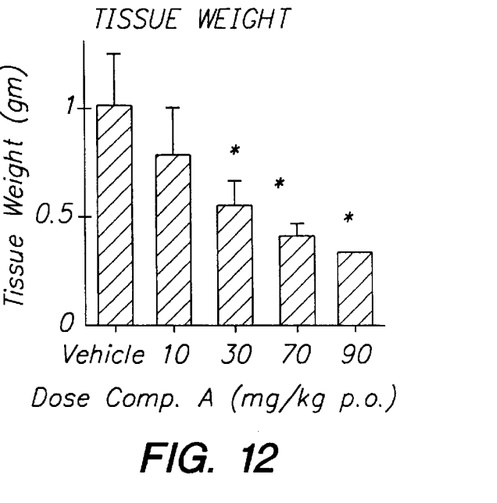
FIG. 12 shows tissue weight as a function of Compound A dose.

In vehicle-treated rats, the TNBS enema stimulated gross morphological damage in the colon and increased the weight of the colonic segments. Compound A elicited a dose-dependent reduction in both the colonic morphological score and wet weight (FIGS. 11 and 12).

Efficacy of Compound A in Supporting Anti-inflammatory Assay

Confirmation of the anti-inflammatory activity of Compound A was sought in another related biological test-the rat adjuvant induced arthritis model of chronic inflammation. This model was selected because almost all of the anti-IBD agents also show efficacy in standard arthritis models. In this model Compound A was tested at 100 mg/kg, po in a 1 % methyl cellulose suspension. On day 0 all animals received an injection of either *Mycobacterium butyricum* (100μL, 20 mg/mL in mineral oil) or mineral oil in the base of the tail. 14 days after this injection, rat paws were measured and all the rats were randomized into 3 treatment groups of 8. A control adjuvant group (group without further treatment), a group to be treated with dexamethasone (steroid reference) and a group to treated with Compound A. Rats received Compound A 100 mg/kg, po, or dexamethasone 0.1 mg/kg, op, daily until day 21 (7 days dosing). On day 21 rats were sacrificed. Paw measurements were taken after 5 and 7 days treatment. The treatment schedule is summarized in the table below.

TABLE 4

Treatment Schedule for an Adjuvant-Induced Arthritis Model of Chronic Inflammation

| Group (n = 8) | Day 0 | Days 14–21 |
|---|---|---|
| Mineral Oil Only* | Mineral Oil | No treatment |
| Adjuvant | Adjuvant** | No treatment |
| Dexamethasone | Adjuvant** | Dexamethasone, 0.1 mg/kg/day op |
| Compound A | Adjuvant** | Compound A, 100 mg/kg/day po*** |

*Vehicle for adjuvant
**Mycobacterium butyricum
***by gavage

Figure 13:
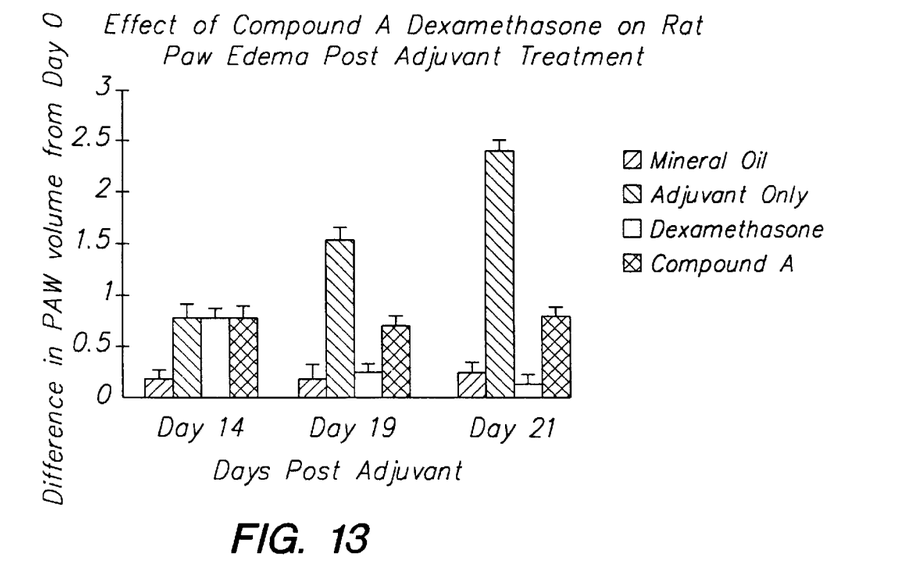
FIG. 13 compares the effectiveness of Compound A with dexamethazone.

In this confirmatory experiment, rats treated with Compound A or dexamethasone showed a significant inhibition of the inflammatory response (p<0.005) compared to those treated with adjuvant. The results of the test are shown in FIG. 13.

Compound N Activity Tests

Compound N was subjected to a series of TNBS activity tests as just described. It exhibited better activity than that of Compound A, showing 75% protection.

Compound N Activity Comparison

The objective of the next experiment was to compare the efficacy of Compound N with orally administered 5-ASA which is currently used in patients with mild-moderate cases of inflammatory bowel disease.

Groups of rats (11 rats/group) were administered Compound N (10 mg/kg po), 5-ASA (10 mg/kg po), 5-ASA (300 mg/kg po), or the methylcellulose vehicle 1 hour prior to the TNBS enema. After 3 days the rats were sacrificed and the colonic damage morphologically evaluated.

Figure 14:
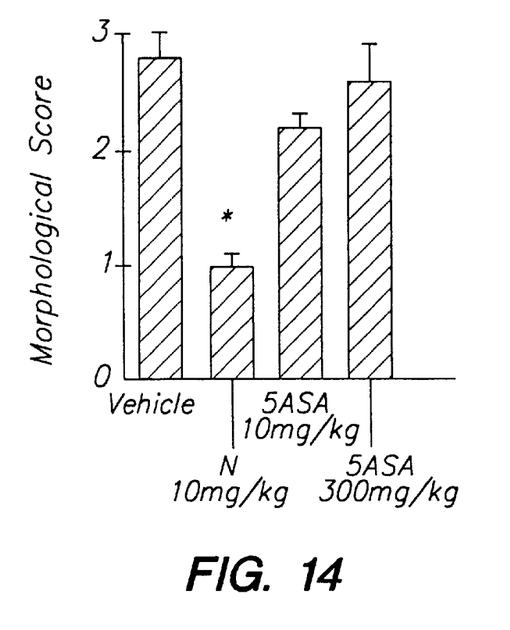
FIG. 14 shows morphological scores comparing Compound N with 5-ASA.

In vehicle-treated rats the TNBS enema induced gross morphological damage. In these same experiments we confirmed that a single oral dose of Compound N give 1 hour before the TNBS enema has excellent efficacy (FIG. 14). However, 5-ASA given orally 1 hour before the TNBS enema had no effect on TNBS-induced colonic inflammation at either dose tested.

Other investigators have shown efficacy with 5-ASA in the TNBS induced model of colitis, however in these studies 50% protection was observed only if multiple high doses were administered intra-rectally.

Dose-Response Characteristics of Compound N in the TNBS model

The objective of this series of experiments was to determine the dose-response curve for Compound N in the TNBS model and evaluate basic pharmacological parameters ($ED_{50}$, $E_{max}$).

Figure 15:
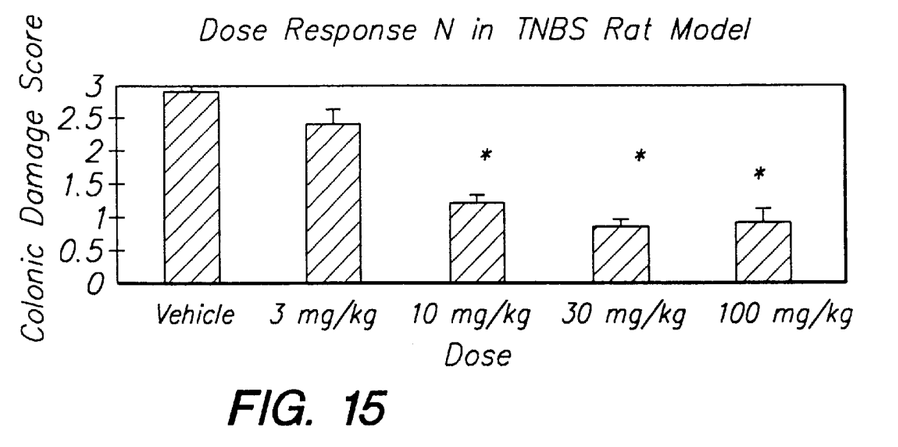
FIG. 15 is a dose response curve for Compound N.

Groups of rats, were administered increasing doses of Compound N (0–100 mg/kg-po) 1 hour prior to TNBS enema. In these experiments the endpoint was macroscopic assessment. The results are given in FIG. 15.

In vehicle-treated rats, the TNBS enema stimulated gross morphological damage in the colon. Compound N elicited a dose=dependent reduction in the colonic morphological score although the protection was only significant (p <0.05) at the 10, 30 and 100 mg/kg doses.

Mouse Dextran Sulfate IBD Model

Another model used for screening candidate IBD-treating compounds is the Dextran Sulfate ("DSS") model. Similar to the TNBS model, DSS induced colitis is widely used as a screening tool for IBD therapeutics. When administered orally, DSS induces IBD-like symptoms in Swiss-Webster mice. This model is used to determine the effectiveness of compounds of this invention when such compounds are administered orally (p.o.)

Individually housed 30–40 g male Swiss-Webster mice (B & K Universal, Fremont, Calif.) received 3% DSS (Sigma Chemicals, St. Louis, Mo.) in their drinking water for 7 days. All animals received food and water ad libitum.

Two groups of mice were dosed orally with either Compound A in a dosing vehicle (1% methyl cellulose, dose range of 10 mg/kg to 30 mg/kg) or dosing vehicle alone (control).

Clinical signs of colitis were assessed by a disease activity index ("DAI") consisting of changes in stool characteristics, fecal occult bleeding and body weight loss. The DAI is very similar to the Crohn's Disease Activity Index used in clinical trials to evaluate new agents to prevent/treat IBD. The DAI data were analyzed using Proc Anova in SAS with a Bonferoni post-hoc analysis, and Model 108 in WinNonlin™ (Professional Version 1.5, Scientific Consulting, Apex, NC) for the $ED_{50}$ and $E_{max}$ values. The wet weight and myeloperoxidase ("MPO") data (collected only on Day 7) were analyzed by Proc TTest in SAS. MPO is a marker for neutrophil infiltration.

DAI Scoring (Daily)
  Stool Characteristic: 0=normal, 2=loose and 4=diarrhea
  Fecal Occult Blood: 0=negative, 2=positive, 4=gross bleeding
  Weight Change: 0=0–1%, 1=1 to <5%, 2=5% to <10%, 3=10 to <20% 4=>20%
  MPO (Day 7 Only)
  Two strips of colonic tissue/mouse
MPO activity by spectrophotometric assay Compound A showed protective effect against DSS-induced colitis. This protective effect was statistically significant on days 3, 4, 5 and 7. A trend toward protection with wet weight and MPO values was observed with Compound A, but the protection was not statistically significant.

The estimated $ED_{50}$, and $E_{max}$ values are approximately 15 mg/kg and 80% protection, respectively. These values are similar to those found with test compounds in the TNBS model.

Establishment of the Dose-response Characteristics in the Mouse Dextran Sulfate Model To determine the dose-response relationship of Compound A in the DSS Mouse Model, the following procedure was used.

Experimental conditions and statistical analyses were the same as the Mouse Dextran Sulfate IBD Model, except four groups of mice (n=8–10/group) were used. Animals were dosed orally with either Compound A (3, 10 or 30 mg/kg) or vehicle alone. In addition, the following procedure was introduced to evaluate the histology in the animals:

Histology Score
  5–6 slices/segment with 15–18 total pieces/colon
  Score for extent of damage: 0=1–25% involvement, 1=26–50% involvement, 2=51–75% involvement, 3=76–100% involvement
  Score for grade:
  0=intact crypt, 1=loss of ⅓ crypt, 2=loss of ⅔ crypt, 3=loss of entire crypt with surface epithelium intact, 4=loss of entire crypt and erosion of surface epithelium
  Score for Severity:
  0=normal, 1=focal inflammatory cell infiltrate including PMNs, 2=inflammatory cell infiltration, gland dropout and crypt abscess, 3=mucosal ulceration
  Single, evaluator (qualified pathologist) blinded to the treatment conditions.

The DAI score showed a marked dose-dependent protective effect Compound A against DSS-induced colitis, which was statistically significant at 30 mg/kg. Protective effect was statistically significant on days 3, 4, 5 and 7. The wet weight and MPO values were significantly increased by the DSS treatment compared to values in the control mouse. A trend toward protection with wet weight and MPO values was observed with Compound A but the protection was not statistically significant.

Effect of Test Compounds on Flux of Reactive Oxygen Species Induced by TNF-α

Oxidative stress agents (OSA) are thought to be involved in cell death in IBD and are key initiator in the cascade of events leading to apoptosis. The purpose of this study is to evaluate the effect of Compound A on cytokine-induced OSA flux.

To visualize OSA, the dye dihydrodichlorofluorescein diacetate is used. This non-fluorescent dye is taken up by cells and deacetylated to its non-fluorescent congener dihydrodichlorofluorescein ($H_2DCF$), which is trapped within cells. Reactive oxygen species ("ROS") react with $H_2DCF$, converting it to the highly fluorescent DCF. DCF fluorescence can be measured spectrofluorometrically and can also be visualized in intact cells using fluorescent microscopy.

SK-N-MC cells (American Type Culture Collection, Rockville, Md.) were plated at 250,000 cells/well in 24-well Corning plates. Following plating, the cells were maintained in retinoic acid medium (5 $\mu$M) for five days and then treated with at test compound at 100 $\mu$M for 1 hour prior to TNF-α (3.0 ng/mL) treatment. TNF-α and $H_2DCF$ were added simultaneously and cultures were incubated for an additional 4 hours. Following incubation, cultures were read in a cytofluorometer at 485–530 nm wavelength to detect increased DCF formation. Relative fluorescence units (RFU) values for the respective treatment conditions were compared. In this assay, higher fluorescence readings indicate ROS production. Thus, reductions in fluorescence indicates reduction in ROS production.

TNF-α treatment resulted in an induction of ROS 2–4 hours after exposure. Incubation of cells with Compound A significantly reduced these effects.

Effect of Compound A on TNF-α Induced Apoptosis in a Human Cell Model

This test is used to evaluate the potential of Compound A to prevent TNF-α induced apoptosis.

Compound A was evaluated in an in vitro model of TNF-α induced toxicity (see Pulliam et al. J. Neurosci. Res. 21:521–530 (1998)). In this model, human brain cell aggregates from fetal tissue were treated with TNF-α which caused an apoptotic cell death. Brain cell aggregates prepared from 1 brain were incubated for 10–12 days before experimentation. Aggregates were weighed out (100 mg/flask) and aliquoted into 10 mL flasks. TNF-α was used at a concentration of 1 ng. Compound A was added 1 hour prior to the TNF-α. Experiments included untreated brain aggregates, TNF-α-treated brain aggregates, TNF-α-+test compound treated aggregates and test compound treated aggregates. After TNF-α was added, aggregates were incubated for an additional 48 h. After this time, brain aggregates were centrifuged for 5 min at 500 rpm. The supernatant was removed and the pellet was lysed for determination of programmed cell death. (Boeringer Mannheim Cell Death Kit ELISA).

In this model, Compound A at concentrations as low as 0.01 $\mu$M was shown to protect against TNF-α induced apoptosis.

Effect of Compound A on TNF-α Induced Reduction in bcl-2

Cytokine mediated apoptosis or programmed cell death is believed to be involved in a number of diseases including IBD. Reductions in bcl-2 are a major signal in initiation of the apoptotic cascade (see Jourd'heuil et al., J. Clin Gastroenterol. 25(Suppl):S61-S72 (1997)). The purpose of this study is to investigate the effects of Compound A on bcl-2 protein levels in a cellular model of cytokine mediated apoptosis.

SK-N-MC cells (American Type Culture Collection, Rockville, Md.) were plated at 500,000 cells/plate and treated with retinoic acid ("RA") (5 $\mu$M) for 5 days. Following RA treatment, the cells were incubated with Compound A (100 $\mu$M) for 1 hour. Cells were then treated with increasing concentrations of TNF-α (0, 0.3 and 3 ng/mL) for 6 h. The cells were harvested and lysed and bcl-2 was measured in the lysate using an ELISA assay (Boehringer Manheim). Quantification of bcl-2 was based on a standard curve and results are expressed as units/mL of bcl-2 in the sample. Results represent mean ±SE for 3 separate cultures.

Compound A at a dose of 100 EM prevented bcl-2 reduction induced by TNF-α doses, of either 0.3 or 3.0 $\mu$g/mL.

What is claimed is:

1. A method of treatment comprising:
   a. identifying a patient suffering from or susceptible to an inflammatory bowel condition; and b. administering to said patient in need thereof an effective inflammatory bowel condition-treating amount of a pharmaceutical composition comprising a benzamide compound of Formula I wherein R' is a saturated alkyl of from 3 to 5 carbon atoms; each R is independently acetamido, nitro or amino; and n is 1 or 2 as active agent.

2. The method of claim 1 wherein said composition is administered orally.
3. The method of claim 1 wherein said composition is administered parenterally.
4. The method of claim 1 wherein said composition is administered rectally.
5. The method of claim 1 wherein said inflammatory bowel condition is ulcerative colitis.
6. The method of claim 1 wherein said inflammatory bowel condition is Crohn's disease.
7. The method of claim 1 wherein said benzamide is selected from the group consisting of:
   N-tert-butyl-4-acetamidobenzamide (Compound A);
   N-iso-propyl-4-acetamidobenzamide (Compound B);
   N-tert-amyl-4-acetamidobenzamide (Compound C);
   N-methylcyclopropyl-4-acetamidobenzamide (Compound E);
   N-iso-propyl-4-nitrobenzamide (Compound F);
   N-tert-butyl-3-nitrobenzamide (Compound G);
   N-tert-butyl-2-nitrobenzamide (Compound H);
   N-n-butyl-4-nitrobenzamide (Compound J);
   N-n-propyl-4-nitrobenzamide (Compound K);
   N-tert-butyl-3,5-dinitrobenzamide (Compound L);
   N-1-methylpropyl-4-nitrobenzamide (Compound M);
   N-tert-butyl-4-aminobenzamide (Compound N);
   N-tert-butyl-3-aminobenzamide (Compound P); and
   N-tert-butyl 4-nitrobenzamide (Compound Q).
8. The method of claim 7 wherein said benzamide is N-tert-butyl-4-acetamidobenzamide (Compound A).
9. A method of treatment comprising:
   a. identifying a patient suffering from an inflammatory bowel condition; and
   b. administering to said patient in need thereof an effective inflammatory bowel condition-treating regimen of a pharmaceutical composition comprising a benzamide compound of Formula I wherein R' is a saturated alkyl of from 3 to 5 carbon atoms; each R is independently acetamido, nitro or amino; and n is 1 or 2 as active agent.

10. The method of claim 9 wherein said regimen comprises one oral dose per day in an amount of from 0.1 to about 150 mg/kg of patient weight.
11. The method of claim 9 wherein said regimen comprises two or three oral doses per day each in an amount of from 0.1 to about 150 mg/kg of patient weight.
12. The method of claim 9 wherein said regimen comprises one intravenous dose per day in an amount of from about 0.01 mg/kg/hour to about 100 mg/kg/hour of patient weight for at least about 1 hour.
13. The method of claim 9 wherein said regimen comprises two or three intravenous doses per day each in an amount of from about 0.01 mg/kg/hour to about 100 mg/kg/hour of patient weight for at least about 1 hour.
14. The method of claim 9 wherein said regimen comprises one rectal dose per day in an amount of from 1 to about 150 mg/kg of patient weight.
15. The method of claim 9 wherein said regimen comprises two or three rectal doses per day each in an amount of from 1 to about 150 mg/kg of patient weight.
16. A method of prophylaxis comprising:
   a. identifying a patient susceptible to an inflammatory bowel condition; and
   b. administering to said patient in need thereof an effective inflammatory bowel condition-treating regimen of a pharmaceutical composition comprising a benzamide compound of Formula I wherein R' is a saturated alkyl of from 3 to 5 carbon atoms; each R is independently acetamido, nitro or amino; and n is 1 or 2 as active agent.

17. The method of claim 16 wherein said regimen comprises one oral dose per day in an amount of from 0.1 to about 150 mg/kg of patient weight.
18. The method of claim 16 wherein said regimen comprises two or three oral doses per day each in an amount of from 0.1 to about 150 mg/kg of patient weight.
19. The method of claim 16 wherein said regimen comprises one intravenous dose per day in an amount of from about 0.01 mg/kg/hour to about 100 mg/kg/hour of patient weight for at least about 1 hour.
20. The method of claim 16 wherein said regimen comprises two or three intravenous doses per day each in an amount of from about 0.01 mg/kg/hour to about 100 mg/kg/hour of patient weight for at least about 1 hour.
21. The method of claim 16 wherein said regimen comprises one rectal dose per day in an amount of from 1 to about 150 mg/kg of patient weight.
22. The method of claim 16 wherein said regimen comprises two or three rectal doses per day each in an amount of from 1 to about 150 mg/kg of patient weight.

* * * * *